(12) United States Patent
McGready

(10) Patent No.: US 6,812,024 B2
(45) Date of Patent: Nov. 2, 2004

(54) ANTI-PARATOPIC ANTIBODY AS AN IMMUNOGEN

(76) Inventor: Roland Keith McGready, 97 Belmont Street, Mosman, New South Whales, 2088 (AU)

( * ) Notice: Subject to any disclaimer, the term of this patent is extended or adjusted under 35 U.S.C. 154(b) by 30 days.

(21) Appl. No.: 09/934,114

(22) Filed: Aug. 22, 2001

(65) Prior Publication Data

US 2002/0192764 A1 Dec. 19, 2002

Related U.S. Application Data

(63) Continuation of application No. 08/887,318, filed on Jul. 2, 1997, now abandoned, which is a continuation of application No. 08/764,283, filed on Dec. 12, 1996, now abandoned, which is a continuation of application No. 08/408,118, filed on Mar. 21, 1995, now abandoned, which is a continuation of application No. 08/291,058, filed on Aug. 15, 1994, now abandoned, which is a continuation of application No. 08/199,964, filed on Feb. 22, 1994, now abandoned, which is a continuation of application No. 07/876,987, filed on May 1, 1992, now abandoned, which is a continuation-in-part of application No. 07/415,354, filed as application No. PCT/AU88/00074 on Mar. 16, 1988, now abandoned.

(30) Foreign Application Priority Data

Mar. 16, 1987 (AU) .............................................. PI 0864

(51) Int. Cl.⁷ ............................. C12N 5/06; C12N 5/16; C12P 21/00; C07K 16/00
(52) U.S. Cl. ...................... 435/327; 435/326; 435/70.1; 435/70.21; 435/70.3; 530/387.2
(58) Field of Search ............................. 435/70.1, 70.21, 435/70.3, 326, 327, 70.2, 346; 530/387.2, 388.35

(56) References Cited

U.S. PATENT DOCUMENTS 4,536,479 A * 8/1985 Vander-Mallie ............. 436/537
4,743,678 A * 5/1988 Essex et al. ................. 530/350

FOREIGN PATENT DOCUMENTS

WO WO 88/07058 * 9/1988

OTHER PUBLICATIONS

Tunkanak et al. Journal of Immunology. 1976; 117 (5), Part 1: 1664–1667.*
Dreesman and Kennedy, J. Infectious Diseases, 151, 761–765, 1985.
Fahey et al., Clin. Exp. Immunol. 88:1–5, 1992.
Fox, Bio/Technology vol. 12, p. 128, 1994.
Kennedy et al., J. Immunology 130, 385–389, 1983.
Kennedy et al., Science 221, 853–855, 1983.
Koprowski, Cancer Research (Suppl.) 45:4689s–4690s, 1985.
Matthews et al., Proc. Natl. Acad. Sci. USA 83, 9709–9713, 1986.
Tungkanak et al., J. Immunol. 117(5):1664–1667, Part I, Nov. 1976.

* cited by examiner

Primary Examiner—James Housel
Assistant Examiner—Shanon Foley
(74) Attorney, Agent, or Firm—Rothwell Figg Ernst & Manbeck

(57) ABSTRACT

The present invention provides a method of manufacture of an anti-paratopic antibody comprising the steps of: (1) selecting from a pool of antibodies occurring in one species a prototypic set the members of which are effective in binding a specific antigen (or antigen epitope), and (2) utilizing one or more members of said prototypic set, or paratopic fragments thereof, as an immunogen in a host of a different species, or in an in vitro incubation system comprising cells derived from the same or a different species, to produce antibodies having a characteristic which is anti-paratopic with respect to said immunogen to produce a synthetic replicate of the specific antigen or epitope. Antigen (or antigen epitope), and monoclonal antibodies, vaccines and processes of immunization employing the product of the method of manufacture are also described.

27 Claims, 8 Drawing Sheets

ANTI-PARATOPIC ANTIBODY AS AN IMMUNOGEN

Figure 1:
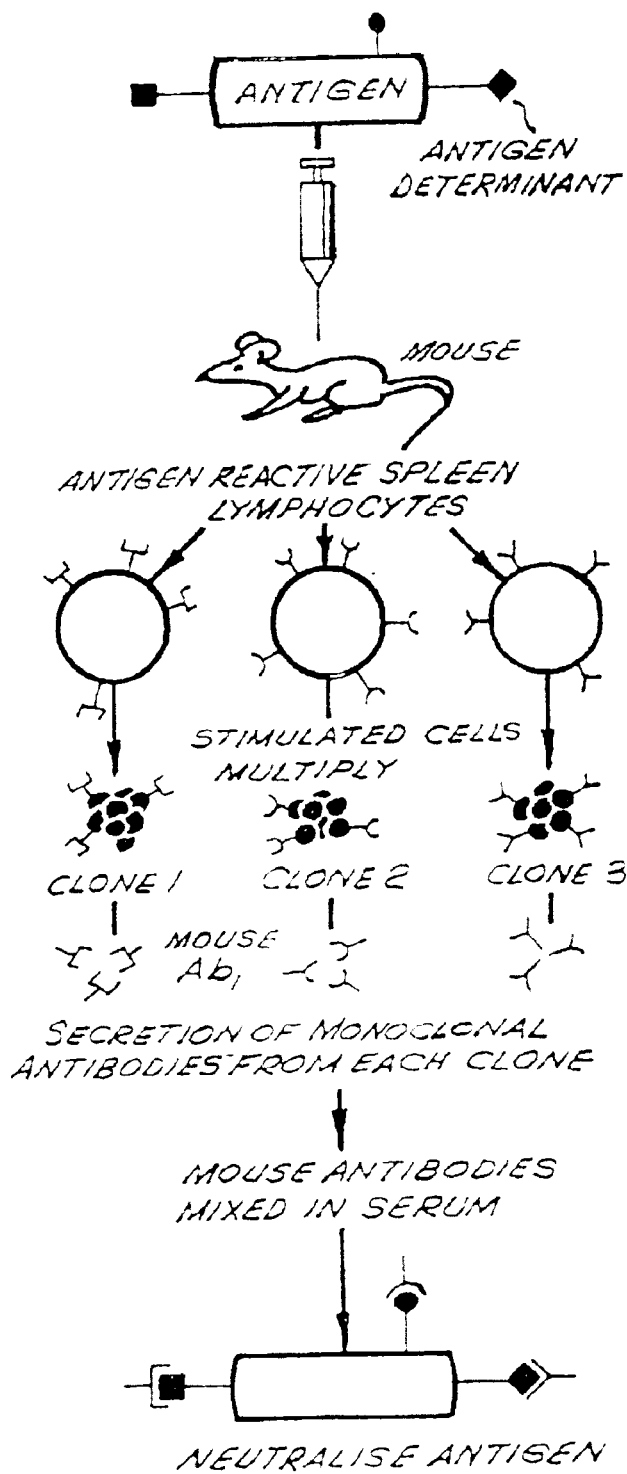

This application is a continuation of Ser. No. 08/887,318 filed 2 Jul. 1997, now abandoned, which is a continuation of Ser. No. 08/764,283, filed 12 Dec. 1996, now abandoned, which is a continuation of Ser. No. 08/408,118, filed 21 Mar. 1995, now abandoned, which is a continuation of Ser. No. 08/291,058, tiled 15 Aug. 1994, now abandoned, which is a continuation of Ser. No, 08/199,964, filed 22 Feb. 1994, now abandoned, which is a continuation of Ser. No. 07/876,987, filed 1 May 1992, now abandoned, which is a continuation-in-part of application Ser. No. 07/415,354, filed 18 Apr. 1990, now abandoned, incorporated herein by reference. Patent application Ser. No. 07/415,354 is a national stage filing under 35 U.S.C. §371 of international application No. PCT/AU88/00074, filed 16 Mar. 1988, and claims priority under 35 U.S.C. §119 to Australian patent application No. PI0864, filed on 16 Mar. 1987.

FIELD OF THE INVENTION

This invention relates to immunology and more particularly to a method of manufacture of immunogenic, compositions, to immunogens manufactured by the method, and to antibodies manufactured therefrom.

BACKGROUND ART

An immunogen is a molecule capable of eliciting an immune response in a vertebrate. The response elicited is believed to be determined by topographical shape characteristics of the immunogen. Immunogens are also called antigens i.e. ANTIbody GENerators because one aspect of the induced response involves the production of antibody molecules whose function is to lock onto the immunogen. Those areas of the immunogen to which the antibody molecule binds are variously referred to as the antigenic determinants, epitopes or haptens. The last term, namely hapten, is generally associated with the term carrier and this term refers to that part of the immunogen/antigen which interacts with cellular components of the vertebrate immune system.

These regions on the immunogen and the names used to define them should not be regarded as absolute. Thus the genus of vertebrates has immune systems which will recognize immunogens; but not all species necessarily recognize the same molecular areas as being haptenic areas or carrier areas. Within a species, the recognition of haptenic molecular areas can only be determined experimentally. Thus, mice will not necessarily process immunogens in the same way as would, for example, the immune system of Man. Furthermore, within a species, individual specimens will not respond to the same degree. This is because the immune response to an immunogen has a genetic (hereditary) component. Thus, some individuals will respond better to an immunogen while others may not respond at all.

The immune response to an immunogen is an integrated phenomenon in that a class of white blood cells called T lymphocytes, for example, reacts with the carrier determinants which in turn allows a class of white blood cells called B lymphocytes to transform and start producing antibodies to the antigenic determinants.

Each cell recognizes only one determinant and each antibody producing B cell (plasma cell) generates only antibody molecules of one given specificity. Hence, the immune system is said to be highly specific. Upon stimulation, these plasma cells multiply and thereby give rise to a clone of identical antibody secreting cells. If it were possible to isolate these identical antibody secreting cells, they would be referred to as monoclonal and the antibodies referred to as monoclonal antibodies.

FIG. 1 is a diagrammatic illustration of the response of a mouse to an immunogen/antigen. Under normal conditions each monoclonal antibody generated by the mouse in vivo mixes with other monoclonal antibodies so that a polyclonal antibody response eventuates.

Each antibody comprises a glycoprotein molecule. The portion of an antibody molecule embodying the characteristic of shape or molecular topography, or code sequence which enables it to bind and so for example neutralise the antigenic determinant or epitope of an antigen is known as a "paratope". The paratope is conceptually a molecular region of a shape complementary to the epitope or to a part of the epitope of the antigen and is thought to reside in the so called hypervariable region of the antibody glycoprotein molecule.

Figure 2:
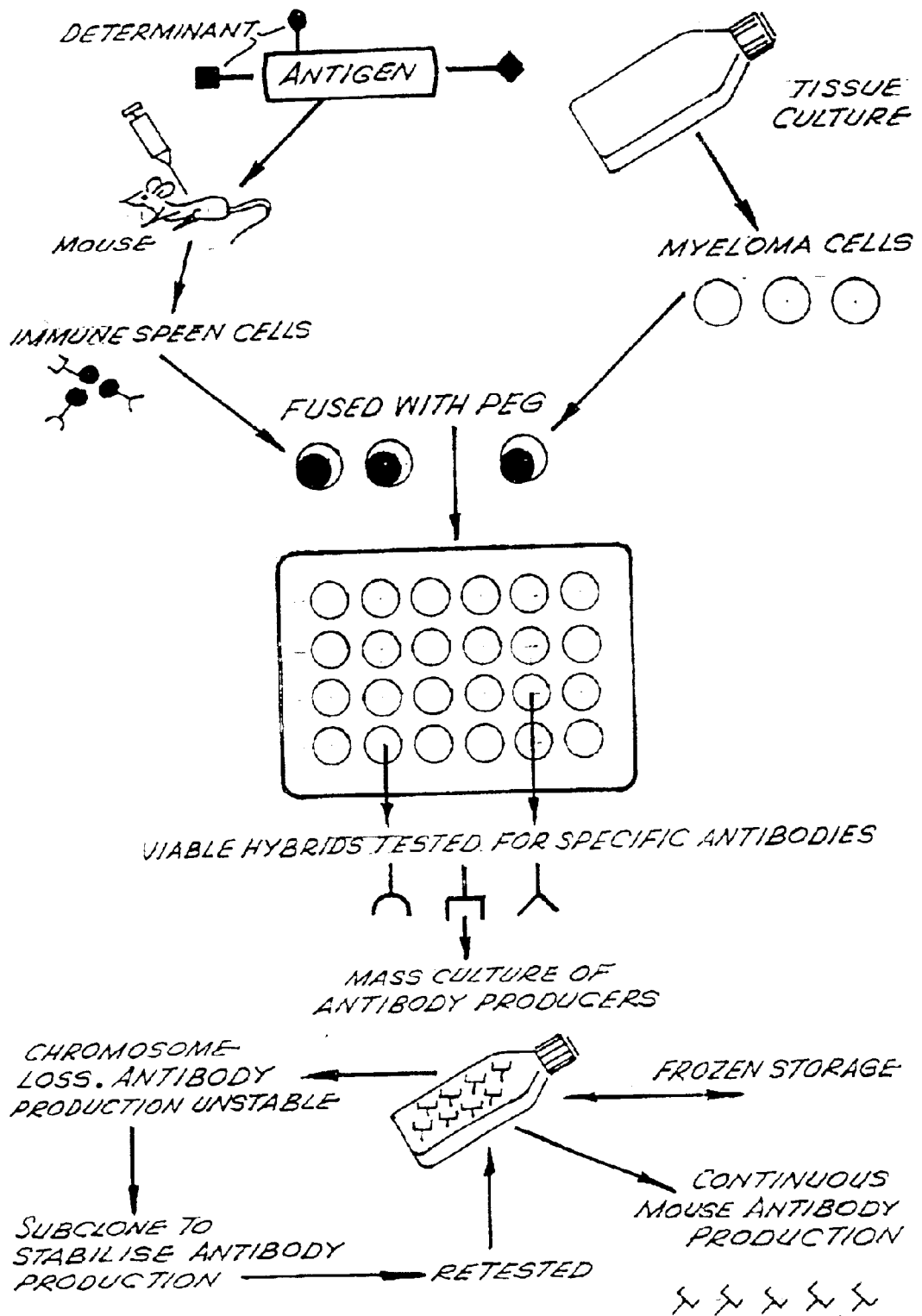

Antibody producing lymphocytes are present in high concentration in the spleen but antigen reactive spleen lymphocytes cannot readily be cultured in isolation. However, monoclonal antibodies may be manufactured and isolated therefrom by use, for example, of techniques of hybridoma technology. In one such technique mice are first exposed to an antigen whereby the mouse develops antibodies. With reference to FIG. 2, spleen cells of the immunised mouse are fused with mouse myeloma cells. The growth of hybrid cells is promoted and the hybrids are screened for specific antibody secretion. Those useful are cultured or undergo further genetic stabilisation procedures. By this means specific monoclonal antibodies may be produced and isolated.

Selected antibodies, or mixtures thereof such as are produced in the method of FIG. 2, may be used to neutralise an antigen in an organism, a paratope of each antibody in effect forming a complex with an epitope of the antigen.

Figure 3:
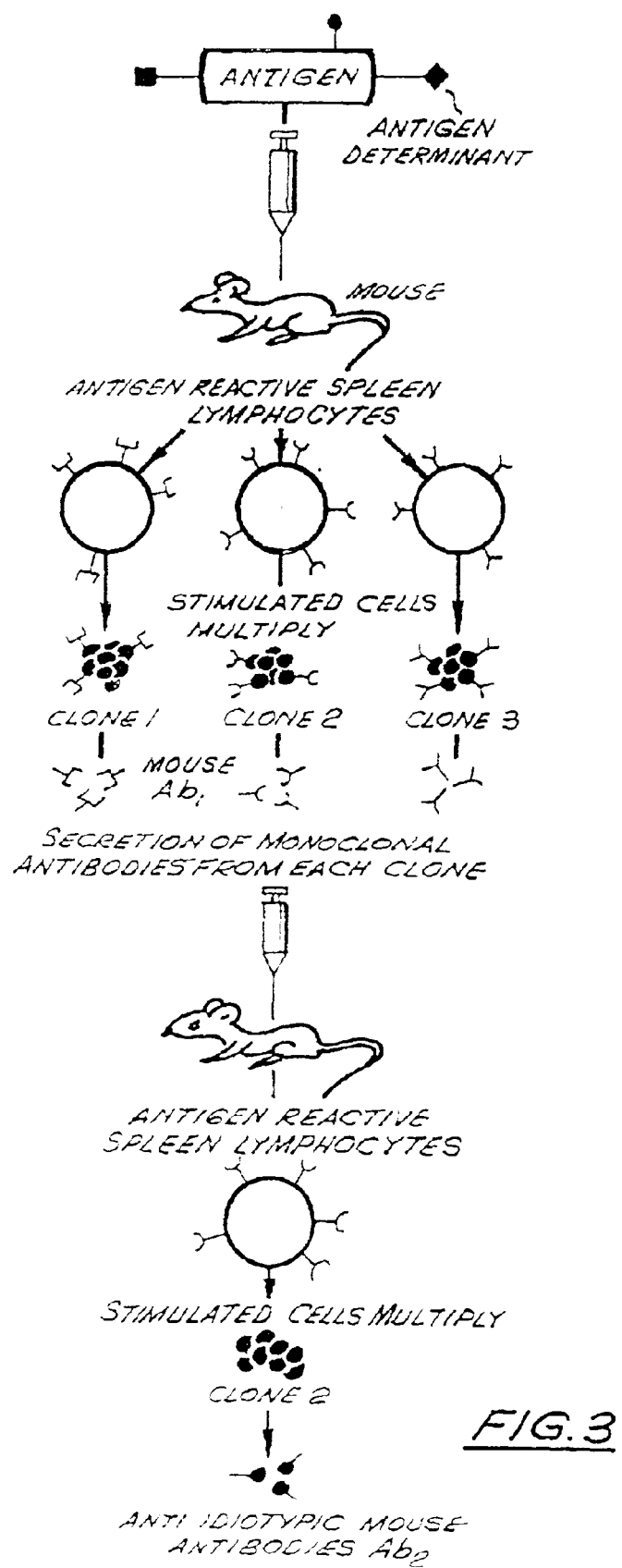

In anti-idiotypic immunology a second stage process shown in FIG. 3 is involved. Mouse 1 is first immunised with an antigen. Thereby giving rise to several clones of antibody producing cells. One cell line is chosen on the basis of the characteristics of the generated antibody and the antibody is referred to as Ab1. Ab1 is then used to immunise a second mouse—mouse 2. The latter must have a genetic constitution very similar to, or identical with that of mouse 1. Mouse 2 generates monoclonal antibodies to Ab1, a subset of which may be directed against the paratope of Ab1. All the antibody subsets generated by mouse 2 against Ab1 may be referred to as Ab2 though the Ab2 subset specific for the paratope of subset 1 is sometimes referred to as Ab2 beta. The second mouse monoclonal antibody, Ab2, has an anti-paratope, that is to say having a molecular portion with a shape characteristic complementary to the paratope of the first antibody. If the epitope of the original antigen is considered to be "mould positive", the paratope of the monoclonal antibody Ab1 can be considered to be a counterpart or "mould negative" and the paratope of the anti-Ab1 antibody that is the paratope of the Ab2 monoclonal antibody can be considered to replicate the "mould positive". It will be understood however that in each case the replication is not exact. When used in a vaccine, the second monoclonal antibody, Ab2, functions as a harmless immunogen which stimulates production of AB3 antibodies in the vaccinated animal effectively producing immunity to the first antigen.

Anti-idiotypic vaccines are designed to be an interspecies approach so as to identify epitopes which induce neutralising antibodies in genetically diverse population. The approach requires that the anti-idiotypic vaccine candidates (Ab2) be inoculated into populations as diverse as sheep, chimpanzees and rabbits followed by antigen challenge to determine if the Ab3 carries the neutralising characteristics of the Ab1. If the challenge is successful Ab1 is further studied as a possible vaccine. If challenge is unsuccessful, the antibody is disregarded for its role as a vaccine. In this approach, the animal studies are meant to simulate the genetic diversity found in Man. The epitopes are therefore exclusively public in that they are capable of generating neutralizing responses in a number of different species.

DISCLOSURE OF THE INVENTION

According to one aspect the present invention consists of a method of treating an animal comprising the steps of:

(1) selecting from a pool of antibodies occurring in a first species of vertebrate a prototypic set the members of which are antibodies with specificity for a specific antigen or antigen epitope expressed in one or more members of the first species, and not expressed in members of a second species;

(2) utilizing one or more members of said prototypic set, or paratopic fragments thereof, as an immunogen in a host of the second species, wherein said second species is selected such that the immune system of said second species does not recognise the specific antigen or antigen epitope uniquely expressed in one or more members of said first species, or said paratopic set or paratopic fragments thereof are utilized as an immunogen in an in vitro incubation system comprising cells derived from the same or a different species, to produce antibodies having a characteristic which is anti-paratopic with respect to said immunogen to produce a synthetic replicate of the specific antigen or epitope.

(3) introducing anti-paratopic antibodies produced in step 2 into the same or a different members of the first species selected in step 1.

According to a second aspect the present invention consists of a method of manufacture of an anti-paratopic antibody efficacious against mammalian infections comprising the steps of:

(1) selecting from a pool of antibodies occurring in a first species of vertebrate a prototypic set the members of which are antibodies with specificity for a specific antigen expressed in one or more members of said first species and not expressed in members of a second species;

(2) utilizing one or more members of said prototypic set, or paratopic fragments thereof, as an immunogen in a host of the second species wherein said second species is selected such that the immune system of said second species does not recognise the specific antigen or antigen epitope uniquely expressed in one or more members of said first species, or said paratopic set or paratopic fragments thereof are utilized as an immunogen in an in vitro incubation system comprising cells derived from the same or a different species to produce one or more antibodies having a characteristic which is anti-paratopic with respect to the antigen or antigen epitope expressed in one or more members of said first species but not expressed in members of the second species; and (3) selecting and purifying said anti-paratopic antibodies produced according to step 2.

In a preferred embodiment of the invention the anti-paratopic monoclonal antibodies are used to immunize a different member of the first species as that from which the prototypic set was selected.

For preference the pool of antibodies consists of naturally occurring human antibodies.

The prototypic set is a set of antibodies selected on the basis of effectiveness against a particular antigen, or epitope thereof, for example is a set of human antibodies selected from humans carrying antibodies resulting from exposure to HIV.

The antibodies, or paratypic paratope bearing segments of them, are utilized as an immunogen in a mouse host to produce mouse antibodies having anti-paratope characteristics.

The mouse antibodies are then screened first for their ability to specifically bind antigens or antigen epitopes in relation to the first species and then in respect of their effectiveness for inducing antibodies which bind the HIV in other members of the first species.

It will be understood that the response generated against the antigen or antigen epitope under consideration would be uncommon in nearly all species except the first species from which the prototypic set of antibodies was selected.

BRIEF DESCRIPTION OF THE DRAWINGS

FIG. 1 is a diagrammatic illustration of the response of a mouse to an immunogen/antigen.

FIG. 2 is a diagrammatic representation of monoclonal antibody production.

FIG. 3 illustrates anti-idiotypic antibody Ab2 production.

FIG. 4 is a schematic representation of the method of manufacture of anti-paratopic antibodies according to the invention.

FIG. 5 (I) illustrated a general procedure for the purification of HIV positive human antibodies.

FIG. 5 (II) illustrates a general procedure for the purification of HIV antigen specific human antibodies.

FIG. 6*a* illustrates purification of human IgG prior to delineation into HIV/HIV antigen specific antibodies.

FIG. 6*b* illustrates purification of human IgA prior to delineation into HIV/HIV antigen specific antibodies.

FIG. 6*c* illustrates purification of human IgM prior to delineation into HIV/HIV antigen specific antigens.

Preferred embodiments of the invention have a number of advantages over the prior art.

Firstly, the invention produces a mouse anti-paratope which is a counterpart of a naturally occurring human antibody paratope for a specified antigen. Upon inoculation the mouse anti-paratope monoclonal antibody produces in a human an antibody bearing a replica of the naturally occurring human paratope.

In the prior art there was produced a mouse anti-paratope which was a counterpart of an artificially generated mouse antibody. Such a mouse anti-paratope monoclonal antibody would produce in a human an antibody bearing a replica of an artificially created mouse paratope (in contrast to a human paratope) and which may not be as effective in binding the specific antigen in a human. In relation to the prior art the invention does not rely upon the assumption inherent within the prior art that the mouse processes antigen in exactly the same way as humans.

Secondly, the present invention has as its basic premise the observation that epitope presentation within a particular species is unique to that species. The prior art technology looks to immuno-dominant epitopes common to all species and aims to produce mirror images to them. Epitopes selected in the prior art technology are identified using empirical approaches and numerous algorithms have been used to predict antigenic sequences. In the present invention, antigenic sequences necessary to produce neutralizing epitopes are believed to be both linear and assembled. Antigen presentation is a multifactorial operation involving several host immune components. Hence, the basic premise of the present invention is that epitope mapping algorithms while applicable do not identify all epitopes of immunological significance. It is in this area which the present invention is focused. The host immune system has a role in the amplification and display of the total repertoire of epitopes of the invading immunogen. The present invention capitalises on this factor whilst prior art technologies have tended to approach the problem from a more conventional anti-idiotypic approach.

Figure 4:
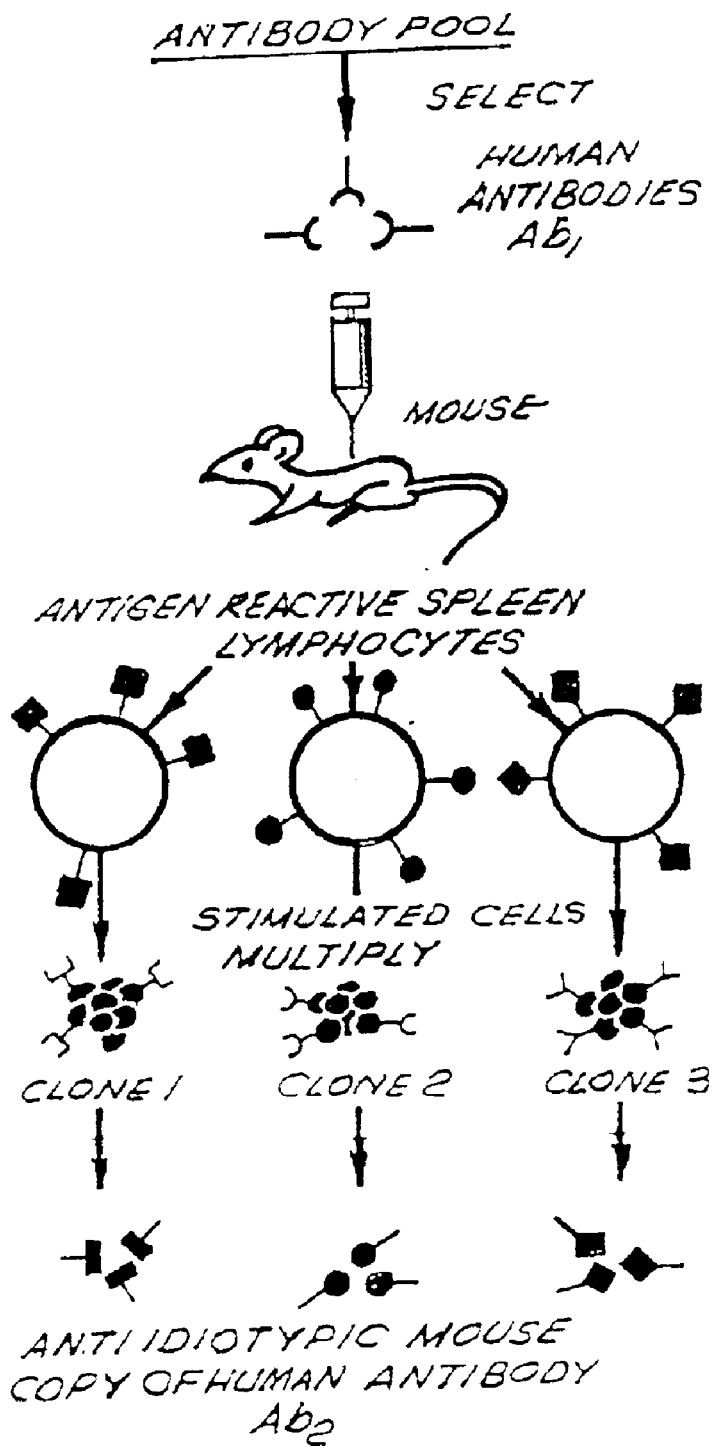
Figure 5:
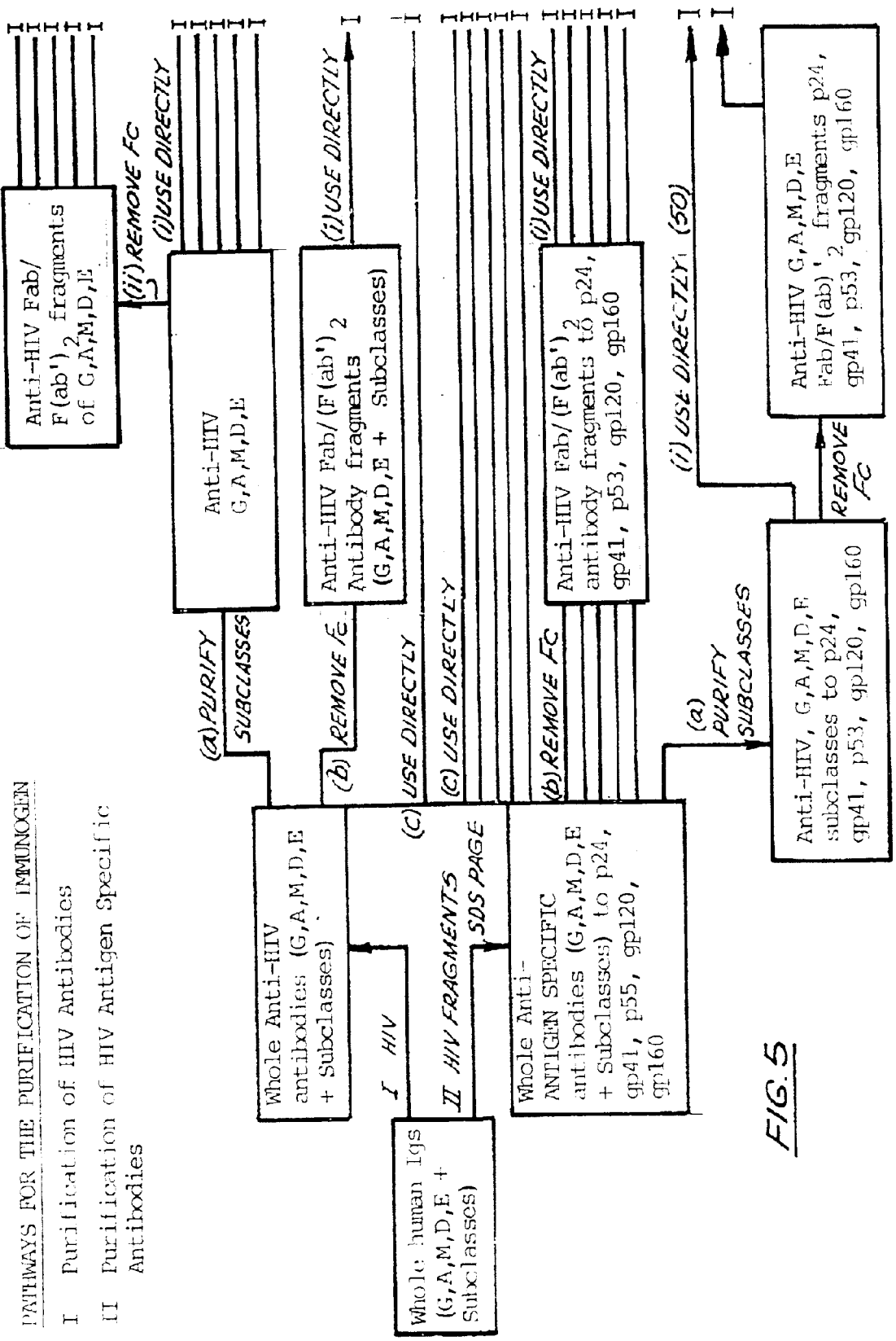
Figure 6A:
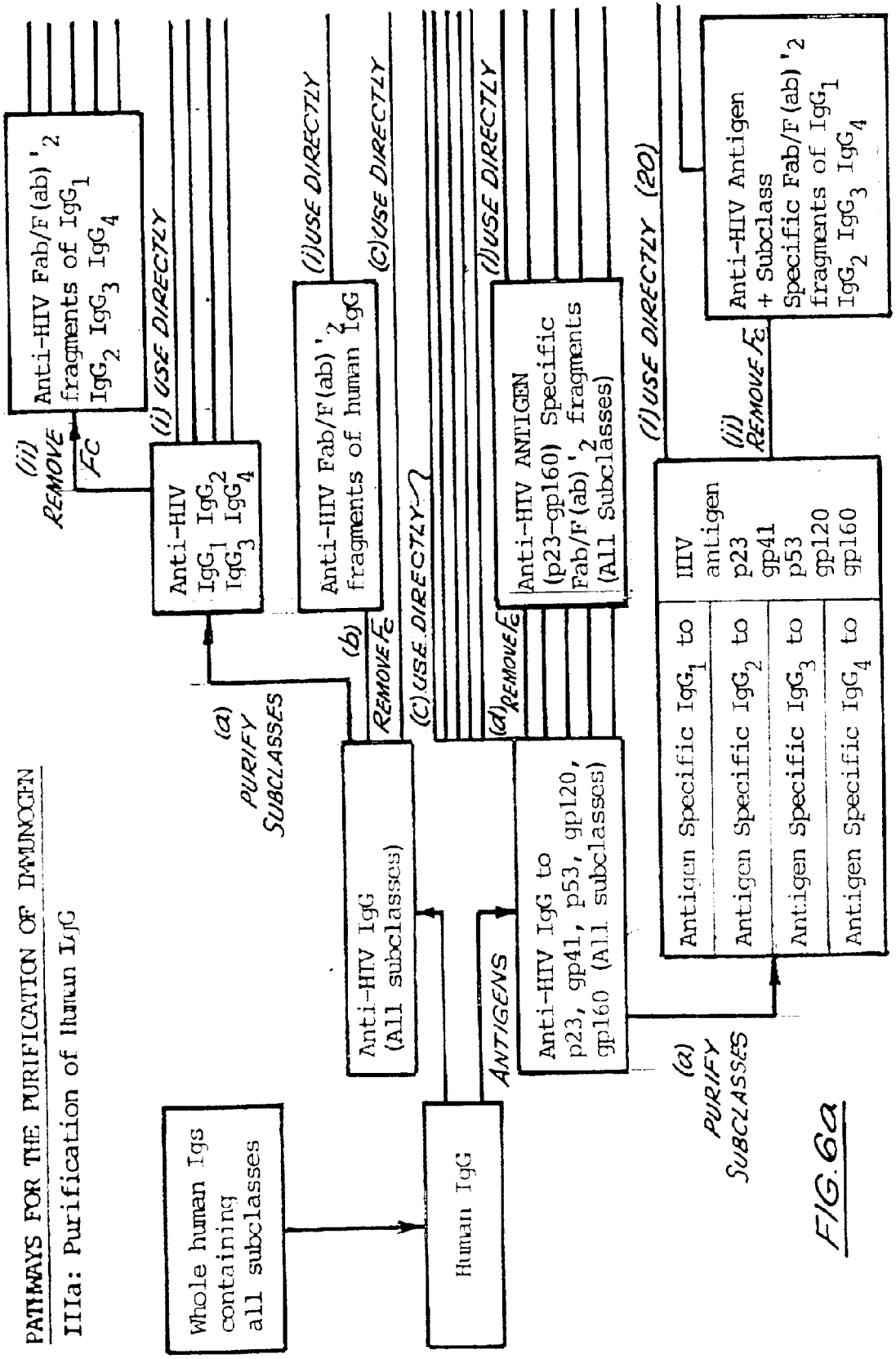
Figure 6B:
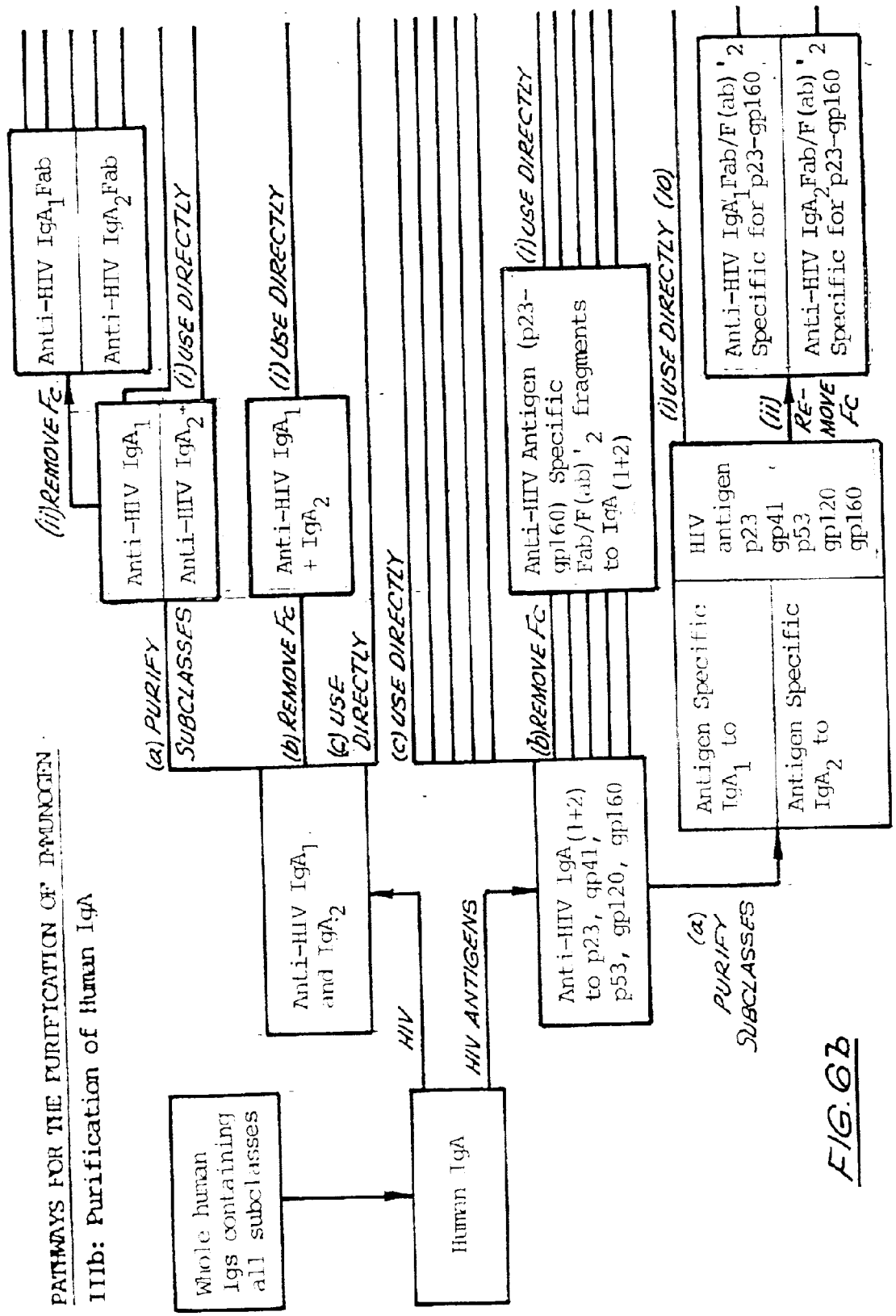
Figure 6C:
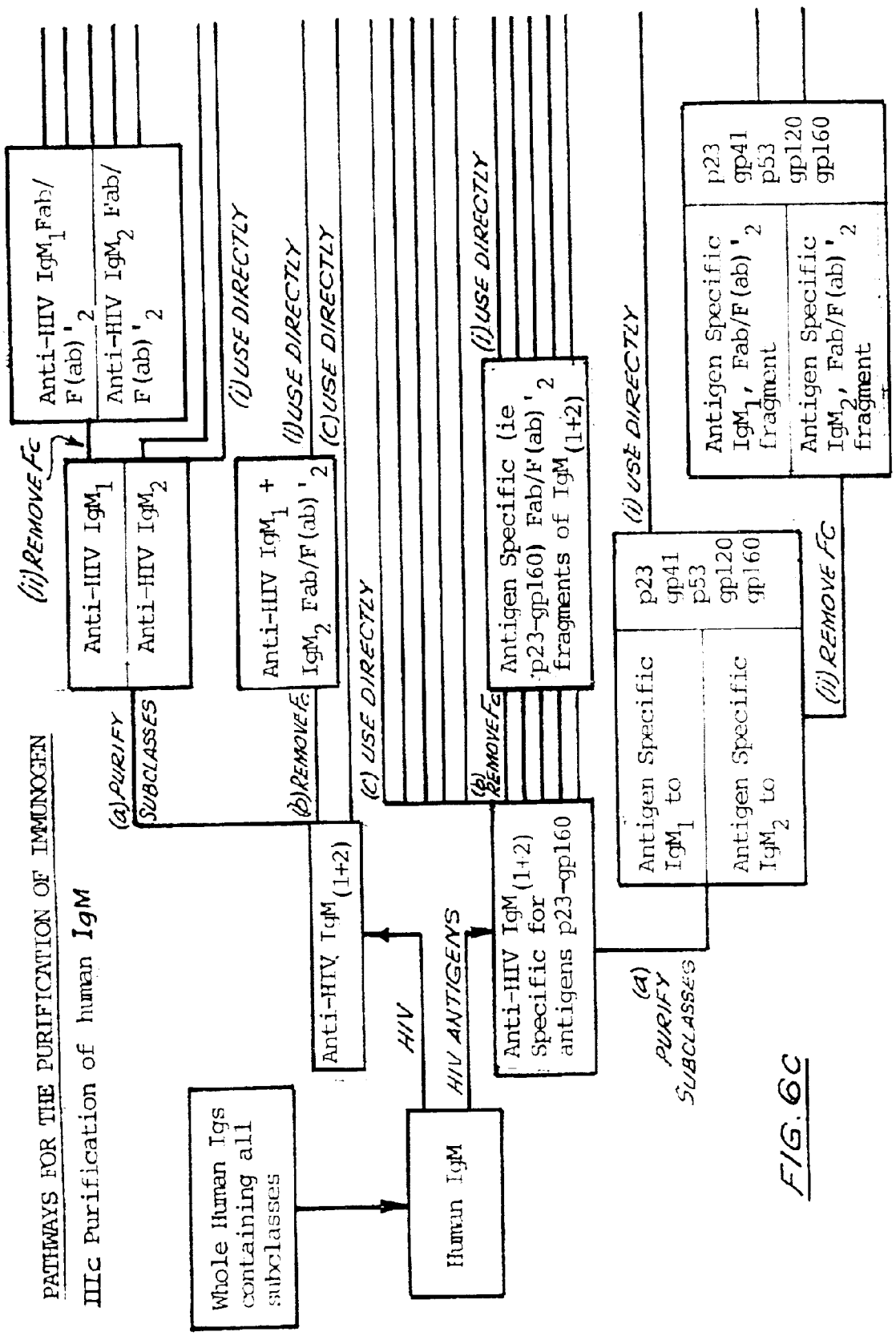

Thirdly, in comparison with the prior art scheme illustrated in FIG. 3, the invention provides a more direct general route shown schematically in FIG. 4 to the production of an anti-idiotypic antibody.

Fourthly, since preferred embodiments of the invention use widely available and naturally occurring i.e. endogenous, antibodies as the starting material rather then antigens, the process is expected to be less costly to conduct.

Fifthly, the process is safer to conduct than processes requiring handling for example of potentially harmful virus antigens.

Finally, both the present invention and anti-idiotypic technology use hybridoma technology, protein chemistry and immunology. When testing the putative vaccine, however, anti-idiotype vaccines have to be tested for complementarity and efficacy in several animal species e.g. rabbits, sheep, baboons or chimpanzees etc. This is necessary to compensate for the interspecies approach used to generate and test the vaccine candidate. This is a relatively long and time consuming step. The vaccine candidate produced in the present invention, however, has to be tested primarily for complementarity within the species to be immunized. It is designed to be primarily an intra-species approach. Accordingly, from a small pool of infected individuals either immune to a particular infectious agent or carrying neutralizing antibodies to it and using standard techniques (or minor technological variants) to produce anti-paratopic antibodies, it is possible using the present invention to generate specific vaccines against said infectious agent. These vaccines can then be used to treat a small number of infected individuals or to immunize an entire population of individuals prone to infection by said infectious agent.

The particular advantage of the present invention is that in the case of some viruses, for example AIDS, there are so many epitopes some of which are protective, some of which are suppressive, some of which are dominant and some which have no effect on the immune system. In the present invention, selection of the antibody is not dependent on the epitope. Instead, selection is based on whether the antibody produced is neutralizing or not. In contrast, in prior art approaches, antibody selection depends on an epitope being common to a variety of different species. For example, if an antibody works in rabbits but not in guinea pigs, it is discarded. The result being to reject it but in doing so, the very epitopes which could protect human populations may be lost. This is overcome by the present invention because reliance is not placed on epitope recognition between species.

BEST MODES OF PERFORMING THE INVENTION

An embodiment of the invention will now be described by way of example only. The embodiment concerns the manufacture of a vaccine to confer immunity against Acquired Immune Deficiency Syndrome (AIDS). The invention is not, however, limited to use for production of any particular vaccine, and has uses other than for the production of vaccines.

The manufacture may be considered as involving the steps of:

(1) selecting a prototypic set of antibodies;
(2) preparing one or more immunogens therefrom;
(3) inoculating hosts with one or more immunogens;
(4) generating a monoclonal antibody pool from each host;
(5) screening the monoclonal antibody pools;
(6) testing the screened antibodies for effectiveness as a vaccine.

In the example under consideration the first stage is to select from the pool of human antibodies a prototypic set, in this case a set of immunoglobulins which effectively bind the aetiologic agent for Acquired Immune Deficiency Syndrome (AIDS). The generally accepted aetiological agent for AIDS is currently known as Human Immunodeficiency Virus hereinafter referred to as HIV.

That is accomplished by obtaining human immunoglobulins from individuals exposed to HIV. About 75% of such individuals have antibodies to HIV.

The antibodies from these individuals are screened for effectiveness in binding HIV antigens and/or antigenic fragments. Those antibodies effective at this function are retained as members of the prototypic set i.e. they are a subset of the pool of human immunoglobulins.

If desired the retained immunoglobulin members so selected may be purified and used directly in step (3).

Preferably, however, in a second step the human immunoglobulins ("Ig") are subdivided into classes G, A, M, D, E (to use the WHO designation) and more particularly identified in Table I.

TABLE 1

PHYSICAL PROPERTIES OF MAJOR HUMAN IMMUNOGLOBULIN CLASS IN SERUM

| WHO Designation | IgG | IgA | IgM | IgD | IgE |
|---|---|---|---|---|---|
| Sedimentation Coefficient | 7S | 7S, 9S, 11S* | 19S# | 7S | 8S |
| Molecular Weight | 150,000 | 160,000 + dimer | 900,000 | 185,000 | 200,000 |
| Number of Ig Units | 1 | 1–2 | 5 | 1 | 1 |
| Number of Antigen Binding Sites | 2 | 2–4 | 10 | 2 | 2 |

TABLE 1-continued

PHYSICAL PROPERTIES OF MAJOR HUMAN IMMUNOGLOBULIN CLASS IN SERUM

| | (gamma) | (alpha) | (mu) | (delta) | (epsilom) |
|---|---|---|---|---|---|
| Identity of Heavy Chain | | | | | |
| Carbohydrates Content | 3 | 8 | 12 | 13 | 12 |
| % Total Immunoglobulin in normal human serum | 80 | 13 | 6 | 0–1 | .002 |
| Concentration range in normal human serum | 8–16 mg/ml | 1.4–4 mg/ml | 0.5–2 mg/ml | 0–0.4 mg/ml | 17–450 mg/ml |

*IgA dimer found in mucosal (secretory) immune system. It is complexed with a secretory component (MW = 60,000) and J chain (MW = 15,000).
IgM contains J chain.
Source: I. M. Roitt, Essential Immunology, 4th Ed. Blackwell 1980

More desirably still the immunoglobulins are further divided into sub-classes, for example, IgG being divided into four sub-classes, IgA being divided into two sub-classes and IgM into two sub-classes. In the preferred embodiment each of sub-classes IgG 1–4, IgA 1–2 and IgM 1–2 are purified and isolated from each other. IgD and IgE sub-classes are present in immunoglobulin in small concentration and their inclusion is optional.

The human IgG/A/M is drawn from three main groups affected by AIDS viral infection, viz male homosexuals bisexual/female/heterosexual AIDS carriers hemophiliacs Blood plasma is heated to 56° C. to kill the virus. Cellular components and serum debris are removed either by aspiration of the serum component or by centrifugation (in the case of plasma).

Human IgG can be purified free of all non-IgG contaminants by affinity chromatography. Other procedures such, as ion-exchange chromatography may be used but affinity chromatography is preferred for speed and selectivity. More particularly, purification is generally effected by means of chromatography using PROTEIN-A SEPHAROSE beads (obtainable from e.g. Pharmacia Biotechnology Pty Ltd.).

Sub-classes of IgG may also be isolated by chromatography.

In a similar manner human IgA purification may be carried out by anti-IgA affinity chromatography.

Human IgM may be purified by a combination of (a) Protamine sulphate chromatography, and (b) Column chromatography, or (c) IgM affinity chromatography.

The purified prototypic immunoglobulins set may be used directly as an immunogen for inoculation of mice in stage 3.

Alternatively, the Ig sub-classes may be screened to select antigen specific antibodies for use as the immunogen. In this case, the Ig sub-classes are next screened for effectiveness against HIV antigen to select the most effective sub-classes in binding the antigen. More preferably, the antigen is first divided into sub-classes known as p18, p24, gp41, p55, gp120 and gp160. These antigen sub-classes differ from each other in molecular structure and can be separated by SDS-polyacrylaniide gel electrophoresis. Each Ig sub-class is then screened against each antigen sub-class to select the most effective Ig's.

TABLE 2

HTLV III - HUMAN SERUM Ig PARATOPE GRID

| Human Serum 1g's* | | 1 gG (80%) | | | | 1 gA (13%) | | | | Antigen Specific |
|---|---|---|---|---|---|---|---|---|---|---|
| HTLV III Antigens | No. of Epitopes | 1 (65%) | 2 (23%) | 3 (8%) | 4 (4%) | 1 (80%) | 2 (20%) | 1 gM (6%) | | Human Paratope |
| | | | | | | | | 1 | 2 | |
| p24 | 2 | | | | | | | | | 16 |
| gp41 | 4 | | | | | | | | | 32 |
| p53 | 5 | | | | | | | | | 40 |
| gp120 | 12 | | | | | | | | | 96 |
| gp160 | 16 | | | | | | | | | 128 |
| Carrier Specific Idiotypes | | 39 | 39 | 39 | 39 | 39 | 39 | 39 | 39 | |
| Total Number per 1 g Class | | | 166 | | | | 78 | | 78 | |
| % Spread of Idiotype | | | 50% | | | | 25% | | 25% | |

*1 gD and 1 gE not included

With reference to Table 2, there is shown a "paratope grid". If it is assumed that there is one antigenic group anchored to a ten thousand dalton-carrier group then the total number of antigenic groups (epitopes) available among the five antigenic sub-classes would be thirty nine. With eight potential antibody classes in the grid that can respond to the thirty nine antigens the total number of possible antibodies carrying paratopes specific for HIV is 312. Put differently, there are on average thirty nine HIV paratopic bearing human immunoglobulins per immunoglobulin sub-class. Thus, for example, it might eventuate that human IgG1 has specificities for all thirty nine epitopes ("haptens"), i.e., there would be thirty nine IgG1 molecules all absolutely identical except for one feature namely their Fab paratope would be different.

In the third step of the embodiment, one or more members of the prototypic set are used as an immunogen in a non-human host for example by being injected into a mouse. The one or more members are preferably the most effective of the immunoglobulin sub-classes. The criteria of effectiveness may be effectiveness against a specific antigen or effectiveness against a spectrum of antigen sub-classes or other criteria.

Human antibodies are excellent immunogens when injected into mice. The antigenic sites on the human antibody molecules are spread right across the length of the molecule from the $NH_2$ terminus-ie the Fab end to the carboxylic acid terminus-ie the Fc end. The Fab $NH_2$ end carries the paratope. Other antigenic components of the Fab are present for structural or "carrier" purposes. For the purposes of the vaccine the Fc exclusively exhibits "carrier" as opposed to paratope antigens.

Immunization studies have demonstrated that not all the antigenic sites on the intact human immunoglobulin molecule are of equal value in that a greater proportion of induced antibodies tend to be directed against the Fe region. This phenomenon is described as antigenic competition or more accurately as intramolecular antigenic competition. When developing an anti-paratopic antibody, however, the part of the molecule of most interest is the Fab area that is to say the paratope bearing region. A simple way to overcome the problem of Fc dominance is to enzymatically cleave the immunoglobulin molecule and isolate the Fab fragment. When used to immunize a mouse this will cause all the induced immunoglobulins to be directed against the Fab fragment. A subset of the anti-Fab antibodies generated by the mouse, irrespective of whether an intact immunoglobulin molecule or a Fab/F(ab)'2 fragment has been used, will be directed against the internal idiotope i.e. paratopic image of the human immunogen. Thus, the member of the anti-HIV prototypic set used as an Immunogen in the mouse may be either (a) the mixed intact human immunoglobulin specific for the AIDS virus, (b) selected classes or sub-classes of the intact immunoglobulin, (c) a Fab/F(ab)'2 fragment of one or a combination of the AIDS specific immunoglobulins or (d) a Fab/F(ab)'2 fragment of one or a combination of the AIDS specific immunoglobulins complexed to carriers eg. Keyhole Limpet Haemocyanin or human albumin.

The stage of preparation of immunogen may thus include enzymatic digestion or chemical cleavage of the human anti-HIV immunoglobulin and conjugation of the Fab/F(ab) '2 to microspheres or the like.

As will be apparent from the foregoing, it is conceivable that when injected into the mouse, the HIV IgG1 subgroup could provide all the relevant paratopes on one type of carrier. This regime would favour the generation of anti-idiotypes in the mouse (as opposed to the generation of anti-"carrier" molecules).

There is a possibility though of inter-molecular antigenic competition so that only a small variety of the human paratopes directed against HIV will end up being antigenic in the mouse. If this occurs then there are various ways of proceeding:

(i) after the screening step those paratopes that are dominant could be isolated from the immunogen population and a second immunization carried out to develop mouse anti-paratope antibodies to the remaining paratopes.

(ii) the anti-idiotypes/idiotypic reagents arising from the first immunization could be screened and tested to see if the anti-idiotypes/idiotypic reagents cover the known HIV antigens/antigenic fragments. If all the known antigens are covered by the generation of anti-idiotypes/idiotypic reagents then a second immunization protocol may not be necessary.

(iii) A different mouse strain could be employed. The eventual manufacturing route thus depends on whether anti-idiotypes/idiotypic reagents to all reagents are required.

It may suffice to have, say, one or two of the haptens from each antigen group covered. To a great extent though, this is an issue that will be resolved by the mouse itself in that it may only be able to raise anti-idiotypes/idiotypic reagents against a restricted idiotype range.

How all these factors are weighted will determine the nature of the immunogen that is preferred for injection into the mouse.

Thus it may be preferable (i) to choose a particular class/sub-class of HIV+ve human immunoglobulin which expresses several specificities and use this to immunize the mouse. Alternatively (ii) given the diversity of the immunoglobulin response the antibody range may not be restricted and a more general immunization routine adopted. In the latter case (iii) sub-class purification may be called for coupled to several primary immunizations.

An excellent starting position though would be to opt for (i) and then remove the Fc prior to further development of the immunogen by linking it to adjuvants such as precipitated immunoglobulins or microspheres.

While stating a preference for (i) an outline of the various alternative pathways for the purification and preparation of the immunogen is shown in FIGS. 5 and 6A–C.

After injection of the immunogen into mice, preferably after a second immunization, mouse spleen cells are harvested by normal methods and fused to NSI in accordance with conventional hybridoma technology.

Hybrids are then grown and screened and positive hybrids cloned and re-tested. The clones are then adapted and grown in serum-free media and specific antibodies purified and ready for testing in human.

The monoclonal antibody pool may be generated using for example the standard method or the "LOTTO" method as outlined in Table 3 below:

TABLE 3

| STANDARD METHOD one-hit | | "LOTTO" (multi-chance) | |
|---|---|---|---|
| | (i) immunize | | |
| (ii) | 4 wks later boost | (ii) | 2–3 days later boost |
| (iii) | 4 days later spleen cell prepn | (ii) | 2–3 days later spleen cell prepn |
| (iv) | Hybridoma productn | (iii) | Hybridize |
| (v) | Preliminary screen | (iv) | Preliminary screen |
| (vi) | CLONE | (v) | Clone |

The Fab pool may be screened by conventional means as shown in Table 4:

TABLE 4

SCREENING FOR FAB POOL

| | Mc Ab Configuration (+Ve/−Ve) | | | | | |
|---|---|---|---|---|---|---|
| Antigen | 1 | 2 | 3 | 4 | 5 | 6 |
| Bence-Jones | + | − | + | − | + | − |
| Human Ig | + | + | − | + | − | − |
| Immunogen | − | − | + | + | − | + |
| ACTION | | | | | | |
| Discard/Retain | D | D | D | D | D | R |

The anti-idiotype pool may be screened by conventional means. For example, HIV on a tray is mixed with human anti-HIV antibodies before and after incubation with mouse HIV idiotype complexed to microsphere/eupergit spheres, then chased with anti-mouse Ig-PO, +Ve is discarded, and −Ve is retained.

Alternatively, HIV on beads is mixed with human anti-HIV PO-enzyme+mouse HIV idiotype +Ve response is discarded.

As will be appreciated by those skilled in the art the antibodies may be selected from a pool occurring in a different species of vertebrate and the prototypic set may be selected from effectiveness against a different antigen. The antibodies may not be free in plasma but may be bound to cells (e.g. B cells) or may exist as immune complex. The prototypic set may be divided into members using different criteria from that exemplified.

Other methods may be used for separation such as use of dyes bound to inert supports, or the use of monoclonal antibodies, etc. and purification of the immunogen without departure herefrom.

The immunogens, or fragments thereof may be utilized in host species other than mice.

The antibodies so obtained may be used in various ways for example for immunization of the vertebrate from which the antibodies were obtained, in test methods and for other purposes.

The invention will now be described more specifically by way of the following Examples.

Preparation of Human Immunodeficiency Virus Specific Human Antibodies

The desired antibody is designated as mouse Ab2. However, the production of mouse Ab2 is dependent upon the prior availability of a first antibody (Ab1) of interest. Presently, there are two sources of Ab1. The first source is the mouse Ab1 produced in vitro, and the second is the human Ab1 to HIV.

There are several good reasons to choose the human Ab1 as the immunogen. Little is known about the epitopes that are relevant in this disease (HIV), other than the identification of the CD4 antigen on the T cell, and those epitopes on the envelope. It has also been postulated that transmembrane proteins may be of importance based on hydrophilicity indices.

The issue about epitopes is that they are primarily linear sequences. Little is currently known about conformational epitopes, neotypes or cryptotopes. A prior knowledge of epitopes of interest is unimportant when human antibodies are being used.

Secondly, the virus is known to be specific for man which is a good reason to use antibodies induced in situ as the starting material to induce the production of the Ab2. It is possible that there are specific epitopes which are of some importance to the human situation which will not be seen in other species.

A. Preparation of Purification of HIV Antigens

Native and recombinant antigens can be purified by affinity chromatography using human antibodies or antibodies from another species such as mouse monoclonal antibodies specific for the HIV antigens. By way of illustration the procedure described will be that using human antibodies. There is very little difference between the two approaches though the benefit is that with the appropriate mouse monoclonal antibodies specific antigens can be purified only if the antigen source is the native one. However, if the antigen source is a recombinant one then human antibodies will allow for the specific purification of the recombinant antigen. When human antibodies are used the steps involved are (1) the preparation of human IgG from HIV infected individuals.

(2) the preparation of the human antibody (IgG) column and (3) the purification of the viral antigens using the aforementioned column.

1. Preparation of Human Antibodies

According to this procedure human antibodies were first purified by either hydroxyapatite chromatography, ion-exchange chromatography (DEAE-cellulose) or protein-A affinity chromatography. By way of example the method for the purification described is that of protein-A agarose column chromatography.

Pooled human sera was obtained from patients positive for the AIDS virus as determined by both an AIDS antibody ELISA assay and subsequently confirmed by the Western Blot assay. Prior to use the serum had been heat treated (56° C. for 30 mins). A 2.0 ml protein-A agarose column was washed with 20 ml of the Monopure binding buffer (Pierce). 4 mls of the pooled serum was diluted with 8 mls binding buffer and centrifuged (200×g:10 min:RT). The supernatant was applied to the column, allowed to percolate through and exhaustively washed in the binding buffer. The human IgG was specifically eluted using the commercially obtained elution buffer (Pierce). Following dialysis and concentration, the $A_{280}$ data was used to determine the concentration of protein which was calculated to be 30 milligrams as determined by the $E^{1\%}=1.43(280\ nm)$. Western Blot and ELISA data confirmed the presence of HIV specific antibodies in the IgG fraction purified in this manner.

2. The Preparation of the IgG Affinity Column 30 mgs of the human IgG was equilibrated in the coupling buffer (0.1M $NaHCO_3$ pH8.3+0.5M NaCl) and mixed with 4 gms CnBr-Sepharose 4B (Pharmacia) which had been pre-washed in 1 mM HCl swollen and equilibrated in the coupling buffer. The mixture was mixed end-over-end in a sealed coupling vessel (2 hrs, RT). Unreactive groups on the matrix were blocked using 0.2 M glycine in the coupling buffer (16 hrs, 4° C.) and the ensuing IgG-Sepharose matrix exhaustively washed in high salt and variable pH buffers prior to the purification of the HIV antigens.

3. The Purification of the Native/recombinant Antigens

By way of illustration, the method described is that for the recombinant HIV antigens in particular recombinant 'gp120'.

Sub genomic clones of HIV cDNA encoding gp120, gp41, p24 and p18 were cloned and amplified in *E. coli* using λ gt11. The *E. coli* lysates were screened with in-house and by commercial HIV antigen ELISA's.

Radioimmunoprecipitation studies confirmed the presence of recombinant HIV antigens and the molecular weights of the recombinant antigens were as predicted e.g. 60 kD for the recombinant 'gp120'.

Following precipitation of E. coli antigens with $(NH_4)_2SO_4$ the supernate was concentrated (Amicon) dialysed against distilled water and then against 0.05M Phosphate buffer pH7.2 (16 hrs, 4° C.). 40 mls of the dialysed concentrate was combined with approximately 2 ml of the IgG-Sepharose and the mixture incubated end-over-end for 2 hrs (RT). The matrix was exhaustively washed and the recombinant protein eluted using 4M $MgCl_2$, pH 8.3. The presence of recombinant antigen was confirmed as outlined above.

B. The Purification of the Human HIV Specific Antibodies

The purification of HIV specific human antibodies involved two steps. These are outlined below.

i The preparation of the HIV antigen column.
ii The preparation of the HIV specific human antibodies.

1. Preparation of the HIV Antigen-sepharose Column 7.5 mls of the eluted protein was mixed with 2 gms swollen, pre-washed and appropriately equilibrated CnBr-Sepharose (pH8.3). The mixture was mixed end-over-end (2 hrs, RT). Unreactive sites were blocked using 0.2M glycine (16 hrs, 4° C.) and the matrix exhaustively washed as outlined for the IgG-Sepharose column.

2. Purification of HIV Specific Human Antibody 4 mls of pooled human HIV serum heat treated as outlined above was passed through a PD-10 column equilibrated with freshly prepared 0.05M Phosphate buffer pH7.2+0.5M NaCl. The first 3 mls fraction (void volume) was discarded and the next 7.5 mls was collected. 10 mls of the gp120-Sepharose matrix and 7.5 mls of the equilibrated serum were mixed end-over-end for 2 hrs at RT. Following extensive washing HIV specific Ig's were desorbed using buffer containing 4M $MgCl_2$ pH8.3. Approximately, 2 mg of HIV specific Ig was obtained using this method.

C. The Production of Mouse Monoclonal Antibody to the Human AB1

The production of Mouse monoclonal antibodies firstly involves the induction of the antibodies either by in vivo methods or by in vitro methods.

By way of illustration the in vitro method is described.

Two groups of Balb/c mice were used in this experiment. The first group consisted of mice which had been tolerized to human IgG1. This had been achieved by injecting mice intraperitoneally, 7 days previously, with 10 milligrams of human IgG1. The second group consisted of untolerized mice.

Mouse Ab2 antibodies were induced in the following way. $1.3 \times 10^8$ mouse spleen cells were recovered and washed in the incubation medium (Iscoves DMEM medium containing 20% foetal calf serum (FCS), 40% thymus conditioned medium (TCM), $5 \times 10^{-4}$ M 2-mercaptoethanol, 4 mM L-glutamine 50 IU Penicillin and 50 IU streptomycin). HIV specific human immunoglobulins at a concentration of 10 micrograms/ml incubation medium was added to the mouse spleen cells. The total volume used in the incubation of the spleen cells with human antibody varied between 10 and 15 mls. In this example, the incubation was allowed to proceed for 7 days in a heated (37° C.) $CO_2$ incubator.

Following incubation the cells were recovered for fusion to either SP2, NS1 or X63-Ag*.653 mouse myeloma cells. The viability of the spleen cells was found to vary between 70 and 99% and the viability of the myeloma was generally 99%. For the sake of illustration SP 2 mouse spleen cells were used though other cells such as rat or human myeloma cells could be used in this procedure. Spleen cells were fused to the myeloma cells using polyethylene glycol 1500/4000 (Boehringer/Mannheim) using standard procedures and following 24 hrs incubation in a $CO_2$ incubator at 37° C. the hybrids were plated out in the incubation medium now containing HAT.

SCREENING OF HYBRID SUPERNATES FOR AB2 SPECIFICITY

Screening for Ab2 was carried out by ELISA. Normal human IgG was coated onto the ELISA trays (1 μg/ml in carbonate-bicarbonate buffer pH 9.6, 4° C., 16 hrs). HIV specific immunogen was coated (0.6 μg/ml) on a separate tray, and mouse supernatants were added in the usual way. Trays were blocked with 2% BSA in PBS-Tween 20 and the color was allowed to develop using ABTS substrate. HIV IgG was also fragmented using Pepsin beads and the trays coated with the F(ab)'2 to further determine the specificity of the mouse Ab2.

In the screening protocol, antibodies obtained from uninfected individuals and HIV-infected individuals were coated onto separate ELISA (screening) plates. If mouse Ab2 bound to both plates it was discarded. If it bound only to the plate containing normal human antibody, it was also discarded. If the Ab2 bound the HIV plate exclusively it was used as a vaccine candidate. Several such vaccine candidates (Ab2) were found.

D. Recovery of Anti-HIV Antibody Clones Produced In Situ as a Result of Natural Infection In addition to the serum HIV antibodies purified by the abovementioned methods it is possible to obtain the human Ab1 by Epstein-Barr virus (EBV) transformation of human B cells obtained from individuals exposed to the AIDS virus.

By way of illustration the following method was used.

Human peripheral blood lymphocytes (PBL's) were diluted 1:1 in phosphate buffered saline and the red cells removed by centrifugation through a Ficoll-hypaque cushion (Pharmacia).

The PBL's either depleted or not depleted of monocytes and lymphocytes using methods familiar to those skilled in the art, were then transformed using for example the EBV isolate B95–8 in sterile tissue culture media (RPMI-1640+ 5% FCS). In a simple example the B95–8 isolate is made available as a supernate which is mixed with the monocyte/T cell depleted fraction enriched for the B lymphocytes. The cells are grown in this mixture, fed as required, and expanded in 96-well flat bottomed plates prior to fusion with the mouse myeloma cell line such as X63-Ag*.653. Screening is by a commercially available HIV antibody ELISA. Cloning and feeding (Medium containing HAT/HT) is by the usual method except that non transformed will be selected out by feeding with 1 micromolar Oubain.

All these methods must be carried out in hybridoma facilities suitable for work involving HIV as virus may be shed under these conditions.

E. Production of Human AB1 Using In Vitro Immunization of Human Peripheral Blood Lymphocytes and/or Splenic Lymphocytes HIV specific human Ab1 may also be obtained by in vitro immunization using whole virus or native, recombinant HIV antigens and antigens bound to nitrocellulose. According to one method $3-4 \times 10^4$ human PBL's or human splenic lymphocytes depleted of monocytes/T lymphocytes using L-Leucine methyl ester can be immunized with small amounts (1 nanogram–10 micrograms) of HIV antigen. The human Ab1 are monoclonal when the techniques of hybridoma technology as outlined in D. are used. Human Ab1 obtained in this way may be used as the immunogen to produce the Ab2 by either in vivo or in vitro culture techniques using human cells or cells of other species as the human Ab1 would house the prototypic paratopes as defined by the foregoing.

Such variations as will be apparent to those skilled in the art from the teaching hereof are deemed to be within the scope of the invention herein disclosed.

What is claimed is:

1. A method of manufacture of an anti-paratopic antibody comprising the steps of:
   (i) selecting from a pool of antibodies prepared from a plurality of humans, a prototypic set wherein members of the prototypic set are antibodies which bind HIV;
   (ii) subdividing the prototypic set selected in step (i) into antibody classes IgG, IgA, IgM, IgD and IgE;
   (iii) screening the antibody classes from step (ii) to select one or more classes which bind at least one of the HIV proteins selected from gp120, gp41, p24, p18, p55 and gp160;
   (iv) introducing one or more of the antibody classes selected in step (iii) into a host of a different species from humans to produce antibodies having characteristics which are anti-paratopic with respect to said introduced antibody and which are a synthetic replicate of the specific antigen or group of antigens used in step (iii); and
   (v) selecting, isolating and purifying the anti-paratopic antibodies produced in step (iv) which bind antibodies that bind HIV.

2. The method according to claim 1, wherein the host used in step (iv) of the method is first tolerized to the class of antibody that is selected in step (iii) before said antibody is introduced into said host.

3. The method according to claim 1 wherein antibodies from the antibody classes selected in step (iii) are enzymatically cleaved to separate F(c) and F(ab) antibody fragments and the F(ab) antibody fragments are used in place of the antibody in step (iv).

4. The method according to claim 1 wherein only those antibody classes that bind two or more of the proteins gp120, gp41, p24, p18, p55 or gp160 are selected for use in step (iv) of the method.

5. The method according to claim 1 wherein only those antibody classes that bind three or more of the proteins gp120, gp41, p24, p18, p55 or gp160 are selected for use in step (iv) of the method.

6. The method according to claim 1 wherein only those antibody classes that bind four or more of the proteins gp120, gp41, p24, p18, p55 or gp160 are selected for use in step (iv) of the method.

7. The method according to claim 1 wherein only those antibody classes that bind all of the proteins gp120, gp41, p24, p18, p55 or gp160 are selected for use in step (iv) of the method.

8. The method according to claim 1 wherein the antibody classes of step (ii) are further subdivided into subclasses prior to performing step (iii) and wherein in step (iii) one or more subclasses are selected.

9. The method according to claim 8 wherein only those antibody subclasses that bind two or more of the proteins gp120, gp41, p24, p18, p55 or gp160 are selected for use in step (iv) of the method.

10. The method according to claim 8 wherein only those antibody subclasses that bind three or more of the proteins gp120, gp41, p24, p18, p55 or gp160 are selected for use in step (iv) of the method.

11. The method according to claim 8 wherein only those antibody subclasses that bind four or more of the proteins gp120, gp41, p24, p18, p55 or gp160 are selected for use in step (iv) of the method.

12. The method according to claim 8 wherein only those antibody subclasses that bind all of the proteins gp120, gp41, p24, p18, p55 or gp160 are selected for use in step (iv) of the method.

13. Purified non-human anti-paratopic antibodies produced according to the method of claim 1.

14. The method according to claim 1 wherein the antibodies produced are polyclonal antibodies.

15. A method of manufacture of an anti-paratopic antibody comprising the steps of:
   (i) selecting from a pool of antibodies prepared from a plurality of humans, a prototypic set wherein members of the prototypic set are antibodies which bind HIV;
   (ii) subdividing the prototypic set selected in step (i) into antibody classes IgG, IgA, IgM, IgD and IgE;
   (iii) screening the antibody classes from step (ii) to select one or more classes which bind at least one of the HIV proteins selected from gp120, gp41, p24, p18, p55 and gp160;
   (iv) incubating the antibody selected in step (iii) with spleen cells derived from either human spleens or from spleens of another vertebrate system for sufficient time to allow the spleen cells to respond to the antibodies;
   (v) preparing from the spleen cell population prepared in step (iv) hybridoma cell lines; and
   (vi) selecting, isolating and purifying anti-paratopic antibodies produced by the hybrids generated in step (v), which bind antibodies that bind HIV.

16. The method according to claim 15 wherein antibodies from the antibody classes selected in step (iii) are enzymatically cleaved to separate F(c) and F(ab) antibody fragments and the F(ab) antibody fragments are used in place of the antibody in step (iv).

17. The method according to claim 15 wherein only those antibody classes that bind two or more of the proteins gp120, gp41, p24, p18, p55 or gp160 are selected for use in step (iv) of the method.

18. The method according to claim 15 wherein only those antibody classes that bind three or more of the proteins gp120, gp41, p24, p18, p55 or gp160 are selected for use in step (iv) of the method.

19. The method according to claim 15 wherein only those antibody classes that bind four or more of the proteins gp120, gp41, p24, p18, p55 or gp160 are selected for use in step (iv) of the method.

20. The method according to claim 15 wherein only those antibody classes that bind all of the proteins gp120, gp41, p24, p18, p55 or gp160 are selected for use in step (iv) of the method.

21. The method according to claim 15 wherein the antibody classes of step (ii) are further subdivided into subclasses prior to performing step (iii) and wherein in step (iii) one or more subclasses are selected.

22. The method according to claim 21 wherein only those antibody subclasses that bind two or more of the proteins gp120, gp41, p24, p18, p55 or gp160 are selected for use in step (iv) of the method.

23. The method according to claim 21 wherein only those antibody subclasses that bind three or more of the proteins gp120, gp41, p24, p18, p55 or gp160 are selected for use in step (iv) of the method.

24. The method according to claim 21 wherein only those antibody subclasses that bind four or more of the proteins gp120, gp41, p24, p18, p55 or gp160 are selected for use in step (iv) of the method.

25. The method according to claim 21 wherein only those antibody subclasses that bind all of the proteins gp120, gp41, p24, p18, p55 or gp160 are selected for use in step (iv) of the method.

26. The method according to claim 15 wherein the antibodies produced are monoclonal antibodies.

27. Purified anti-paratopic antibodies produced according to the method of claim 15.

* * * * *